United States Patent [19]

Lillegard et al.

[11] 4,211,380
[45] Jul. 8, 1980

[54] UNIVERSAL HOSPITAL BRACKET

[75] Inventors: Thomas R. Lillegard, Crystal Lake; Richard A. Rollins, Mundelein; Ronald C. Stauber, Hawthorn Woods, all of Ill.

[73] Assignee: Baxter Travenol Laboratories, Inc., Deerfield, Ill.

[21] Appl. No.: 946,590

[22] Filed: Sep. 28, 1978

[51] Int. Cl.$^2$ .............................................. A47B 96/06
[52] U.S. Cl. .................... 248/229; 24/81 H; 248/224.2; 248/316 B
[58] Field of Search .................. 248/225.4, 229, 226.4, 248/316 B, 225.1, 222.1, 223.4, 224.2, 224.1, 226.2; 24/248 E, 81 R, 81 H, 81 LC

[56] References Cited

U.S. PATENT DOCUMENTS

| | | | |
|---|---|---|---|
| 483,963 | 10/1892 | Leger | 248/316 B X |
| 661,677 | 11/1900 | Taylor | 248/316 B |
| 1,307,011 | 6/1919 | Kohn | 248/316 B |
| 1,394,788 | 10/1921 | Potstada | 248/229 |
| 2,156,025 | 4/1939 | Paul | 248/224.2 X |
| 2,212,156 | 8/1940 | Erdley | 24/81 LC |
| 2,269,790 | 1/1942 | Sherrill | 24/81 LC X |
| 2,473,908 | 6/1949 | Rubin | 248/224.1 X |
| 2,638,301 | 5/1953 | Smith | 248/229 |
| 3,797,792 | 3/1974 | Huber | 248/313 X |
| 4,132,380 | 1/1979 | Pastore | 248/224.1 |

FOREIGN PATENT DOCUMENTS

| | | | |
|---|---|---|---|
| 170968 | 9/1951 | Austria | 248/316 B |
| 334047 | 11/1958 | Switzerland | 248/316 B |

*Primary Examiner*—J. Franklin Foss
*Attorney, Agent, or Firm*—Paul C. Flattery; Gerald S. Geren

[57] ABSTRACT

There is disclosed herein a universal clamp assembly for use in supporting and grasping medical appliances. The assembly includes a housing having means at one end for securing the assembly to a pole or other support. A pair of replaceable opposed arms extend outwardly from the other end of the housing and define a jaw for grasping the appliance. Each of the arms includes pivot means for pivotally securing the arms to the housing and permitting the arms to be moved between open and closed positions. Biasing means are positioned in the housing to cooperate with the arms to resiliently bias the arms toward a closed or grasping position which gives the jaws a snap action.

The arms and biasing means are mounted for rotation about the longitudinal axis of the housing so as to permit positioning of the appliances at various attitudes which is desirable in debubbling a dialyzer. Furthermore, each of the arms is replaceable so as to permit use of the assembly with various types of appliances.

An interlocking bracket and auxiliary clamp construction is also provided for securing auxiliary appliances to the universal clamp assembly. The bracket includes a pair of outwardly diverging ear-like members having shaped outer surfaces. The clamp includes a connector end having a pair of converging ears which are shaped for mating and releasable engagement with said bracket ears.

15 Claims, 9 Drawing Figures

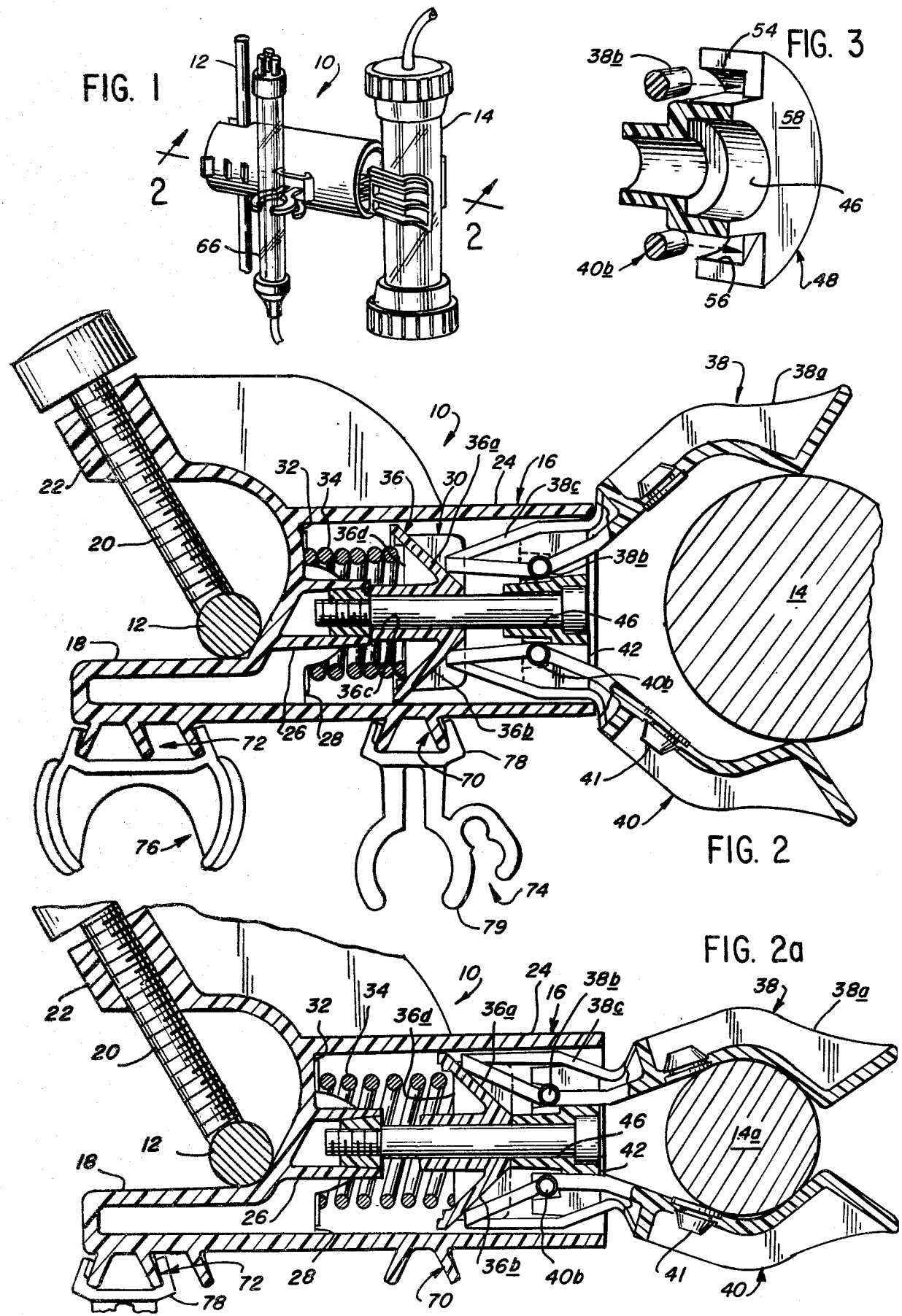

UNIVERSAL HOSPITAL BRACKET

BACKGROUND OF THE INVENTION

This invention relates to clamp assemblies, and more particularly, to an assembly for use in a medical environment to support various medical appliances.

In medical environments, such as hospitals and clinics, IV (intravenous) poles and masts are used to support various types of medical appliances, dialyzers, reservoirs, bottles, etc., which are used in the treatment of patients.

In kidney dialysis, a dialyzer may be supported from an IV pole, and it is desirable to selectively position the dialyzer at various heights and attitudes in both the horizontal and vertical planes.

There is presently available a dialyzer clamp assembly which has a pair of rotatable jaws for receiving a dialyzer. The jaws will only accept dialyzers within a small range of sizes and the jaws are rotatable to specific detented positions. The jaw and detent mechanisms are complex, and include many parts and are difficult to assemble, clean or service. Furthermore, the clamp assembly is mounted to the IV pole in an off-center position which causes the clamp to be particularly susceptible to inadvertent rotation about the pole. This clamp is also provided with an auxiliary mounting system for positioning bubble trap, and the like, above the clamp assembly itself. It has been determined, however, that it is desirable to position the mid-height of the bubble trap at about the same level as the mid-height of the dialyzer.

It is therefore an object of this invention to provide a simple and economically constructed clamp assembly having jaws which can accept a wide range of dialyzer sizes, which can be mounted to an IV pole so as to avoid inadvertent rotation, and which includes an auxiliary mounting system for aligning the bubble trap or other auxiliary appliances with the mid-height of the dialyzer.

It has also been determined that hospitals, clinics, etc. normally stock many different types of clamp assemblies in order to be able to support the various types of appliances used in a hospital.

It is also desirable to provide a clamp assembly which is suitable for use with dialyzers and other medical appliances of differing sizes and shapes so as to minimize the number of clamps which must be stocked and/or purchased by the hospital or clinic.

There are also other bracket-like assemblies known for use with IV poles. See, for example, U.S. Pat. Nos. 3,318,457 and 3,797,792. An adjustable bracket for grasping a drainage bottle and positioning it beneath the bed is also disclosed in U.S. Pat. No. 2,464,672. None of these devices are deemed to be desirable for use in dialysis apparatus and include the disadvantages discussed above.

These and other objects of this invention will become apparent from the following description and appended claims.

SUMMARY OF THE INVENTION

There is disclosed herein a clamp assembly which meets the foregoing objects.

The assembly includes a housing and means positioned in line with the axis of the housing for securing the assembly to an IV pole. The assembly also includes two retainer arms extending from the other end of the housing and forming a jaw for clamping medical appliances, such as a dialyzer or other devices falling within the size range and being somewhat cylindrical in shape.

The arms are pivotally mounted in the housing so that the jaw may be opened and closed with a snap-in-and-snap-out operation. Biasing means are provided within the housing for cooperation with the arms to urge them toward a closed or clamping position. Each arm is identical, and the arms are replaceable so that, depending upon the particular appliance to be used, different arms can be selected for use with the same housing and internal mechanism. Since only the arms need to be replaced for each different situation, the cost of manufacture and use is minimized.

The biasing means and arms are cooperatively positioned in the housing so as to be rotatable about the longitudinal axis of the housing so as to provide for positioning of the dialyzer at the various attitudes.

Auxiliary mounting brackets are molded to the clamp assembly housing and are shaped so as to releasably receive and support an auxiliary clamp assembly which will hold an auxiliary medical appliance substantially in line with the dialyzer. This assures positioning of the bubble trap mid-height in line with the dialyzer height.

BRIEF DESCRIPTION OF THE DRAWINGS

FIG. 1 is a perspective view showing the clamp assembly mounted to an IV pole and supporting a dialyzer;

FIG. 2 is a cross sectional view taken substantially along line 2—2 of FIG. 1 showing the arms and housing with the jaw shown in an open position and about to grasp a dialyzer;

FIG. 2a is a view similar to FIG. 2 and showing the retainer arms clamping a smaller diameter dialyzer;

FIG. 3 is a perspective and sectional view showing the pivot mounting for the retainer arms;

DESCRIPTION OF THE PREFERRED EMBODIMENT

The Clamping Assembly

Figure 4:
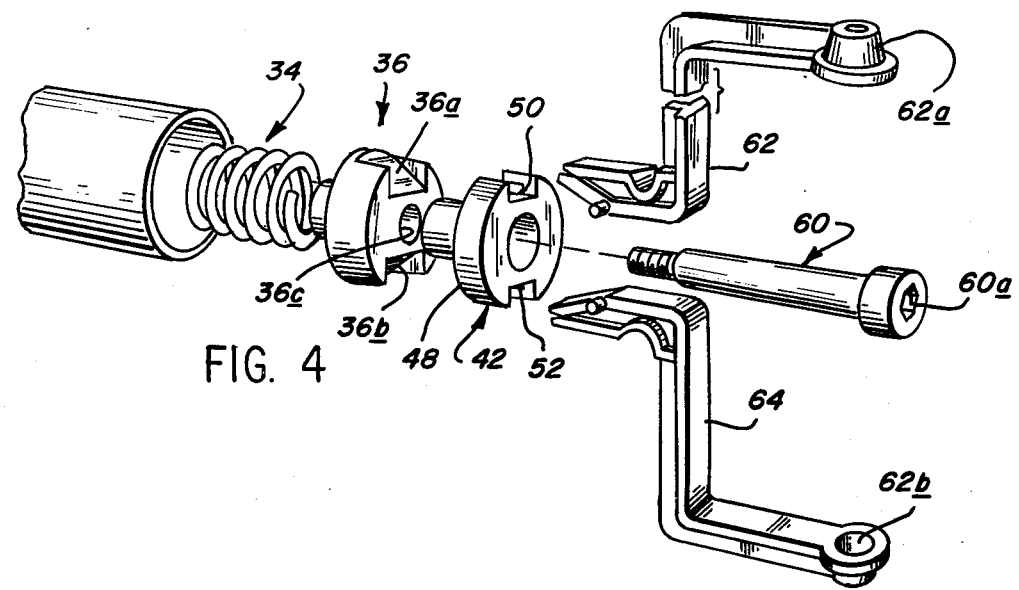
FIG. 4 is an exploded perspective view showing the biasing assembly and a second type of replaceable retainer arms.

Referring now to the drawings, there is shown a clamp assembly 10 generally, mounted at one end to an IV pole 12 and holding a cylindrically-shaped hollow-fiber-type dialyzer 14 at the other end.

The clamp assembly 10 generally includes a molded plastic housing 16 which has a U-shaped section 18 at one end for cooperation with the IV pole 12. A threaded knob 20 extends through a threaded boss 22 in one leg of the U-shaped section 18 and engages the IV pole 12 and securely positions the pole 12 against an inner corner or bight-like portion of the U-shaped section 18. It will be noted that the IV pole is held in a position substantially aligned with the housing so as to minimize inadvertent rotation.

The housing 16 also includes a hollow cylindrically-shaped body or outer portion 24, an internal threaded boss 26 which extends from the U-shaped section 18, and a shoulderlike section 28 molded integral with the boss 26 and body portion.

A spring-biasing assembly 30 generally is positioned within the cylindrical housing 24. The assembly includes a stainless steel washer 32 which seats against the shoulder 28 and surrounds the boss 26. A coiled, stainless spring compression spring 34 is seated at one end against the washer 32 and is also positioned about the boss 26. A disc-shaped cam member 36 having sloped camming ramps 36a and 36b is provided for axial movement within the housing and cooperation with the spring 34. The cam member also includes a cylindrical guide bore 36c and a spring-engaging shoulder 36d.

A pair of identical molded plastic retainer arms 38 and 40 are also provided. Each arm includes an outer appliance-retaining or grasping portion, such as 38a, an integrally molded pivot pin, such as 38b, on each side of the arm, and an internal cam-engaging section 38c.

A disc-like pivot 42, as seen in FIGS. 3 and 4, is provided for pivotal connection to the arm and for receiving the pivot pins, such as 38b, so as to permit pivoting motion of the arms, such as 38, with respect to the housing. The pivot includes a stepped-shaped cylindrical shaft-receiving bore 46 and a generally circular or disc-like section 48. Two opposed notches 50 and 52 are provided in the disc-like section 48 for receiving the arms 38 and 40 and for permitting pivotable motion thereof. The disc-like section 48 also includes four (4) pivot pin-receiving recesses, such as 54 and 56, as seen in FIG. 3. It will be understood that there are four (4) such recesses with two (2) on either side of the notches 50 and 52. The recesses are open from the back so that the arm and its pivot pins may be positioned rearwardly of the notch and moved forwardly until the pins seat in the recesses and are retained in the recesses by the front wall 58 of the pivot. The step-like shape of the shaft-receiving bore 46 is best seen in FIG. 3.

A stainless steel guide shaft and assembly screw 60 is provided and has an enlarged head at one end and threads at the other end. The shaft extends through the bore 46, through the bore 36c in the cam 36 and is threadably received in the boss 26. The head includes a hexagon-type socket 60a for tightening the shaft on the boss 26.

In order to assemble the clamp assembly, the shaft 60a is grasped and held in an upright position. The pivot 42 is dropped onto the shaft, and the arms 38 and 40 are then fitted into the notches and the pivot pins into the recesses. Thereafter, the cam 36 is slipped onto the shaft, spring 34 is positioned onto the shaft, and the washer 32 is fitted onto the shaft. Then the housing is placed over the parts and the socket tightened. The spring 34 then urges the cam 36 toward the arm end of the housing, and the ramp portions 36a and 36b engage the cam-engaging sections or inner arm portions, such as 38c, causing them to move, thereby causing the outer arm sections, such as 38a, to pivot toward each other about the pivots, such as 38b and 40b.

The action of the spring pressure is the only force holding the arms in any given position. This cooperates in providing the desired 360° rotational positioning for the arms and dialyzer.

In order to install the dialyzer on the clamp assembly, a dialyzer, such as 14, is pushed between the arms causing the retainer arms to pivot outwardly against the spring bias and then back inwardly to grasp the dialyzer. The action of the spring bias and the shape of the arm provide for a snap-in-and-snap-out action, which securely holds the dialyzer. Friction pads, such as 41, can be provided on the internal surface of the arms to prevent slippage of the grasped appliance in a transverse direction with respect to the arms.

As can be seen, there is an axis of rotation about the shaft 60, which axis is generally transverse to the axis about which the arms pivot, as well as the axis of the IV pole 12. By grasping and rotating the arms, the arms, pivot 42 and cam 36 are caused to rotate about the shaft 60. The stainless steel washer 32 protects the plastic shoulder 28, and the spring 34 provides the frictional force which holds the arms at the desired angular attitude.

With reference to FIG. 2a, it will be seen that the same clamp assembly and arms can cooperate to hold a smaller diameter dialyzer or device 14a.

Figure 5:
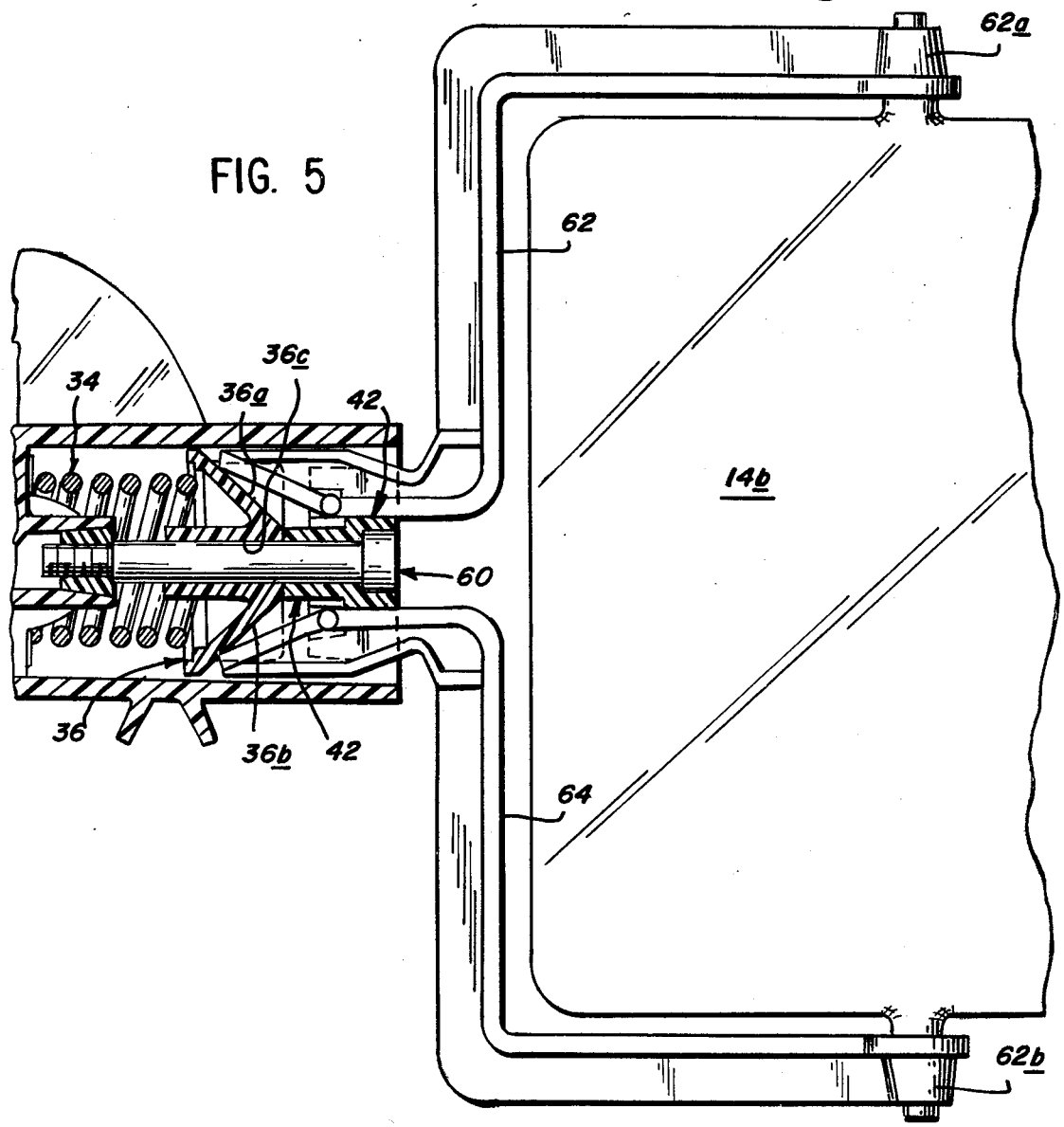
FIG. 5 is a sectional view somewhat similar to FIG. 2, showing the second type of retainer arm construction and a portion of the clamp housing.

With regard to FIGS. 4 and 5, it will be seen that wider and step-shaped retainer arms 62 and 64 can be used. The arms have the same construction for their inner portion and pivot pins, but have differently shaped and wider retainer arms. The arms 62 and 64 include pivot cups 62a and 64a at their outer ends for receiving a medical appliance 14b, which is pivotable about an axis through the cups 62a and 64a. As can be seen in FIG. 5, the biasing assembly cooperates with the inner ends of these arms in exactly the same manner as the arms in the preceding description.

Side-Mounting Clamp Assembly

Figure 6:
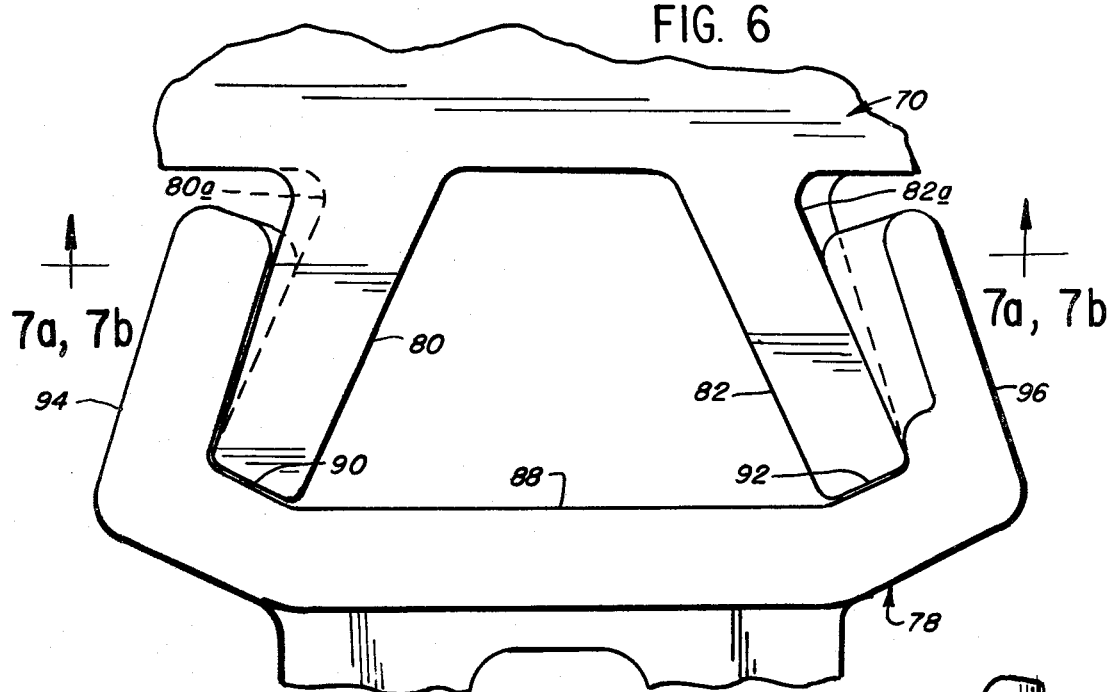
FIG. 6 is a greatly enlarged top view showing the auxiliary bracket and the connector portion of the auxiliary clamp.

Referring to FIG. 1, it is seen that an auxiliary appliance, such as a bubble trap 66, can be mounted on one side of the assembly, with the mid-height of the bubble trap being aligned with the mid-height of the dialyzer. Integral brackets, such as 70 and 72, as seen in FIGS. 1, 2, 6 and 7, are molded integral with the body 24. The bracket 70 includes two outwardly flaring ears, which are best seen in FIG. 6, and the bracket 72 includes three outwardly flaring ears. Auxiliary appliance clamps, such as 74 or 76, are provided for mounting on the brackets 70 and 72. Each clamp, such as 74, has at one end a connector, such as 78, and at the other end an appliance grasping section 79. The clamp 76, although wider than the clamp 74, is similarly constructed. The clamp 74 can be mounted on the bracket 72 using only the inner and the outer bracket ear to its left.

Furthermore, the brackets 70 and 72 are constructed such that they will cooperate with auxiliary clamps if the main assembly is positioned as it is shown or is rotated 180° about its longitudinal axis so that the clamp assembly is, in effect, on the other side of the pole 12.

Referring now to FIG. 6, it is seen that the bracket assembly 70 includes two outwardly flaring or diverging ears 80 and 82. The ears 80 and 82 have generally smooth interior surfaces, but each of the outer surfaces includes an interlocking recess. The shapes of the outer surfaces can be thought of as one being an inverted mirror image of the other.

Figure 7A:
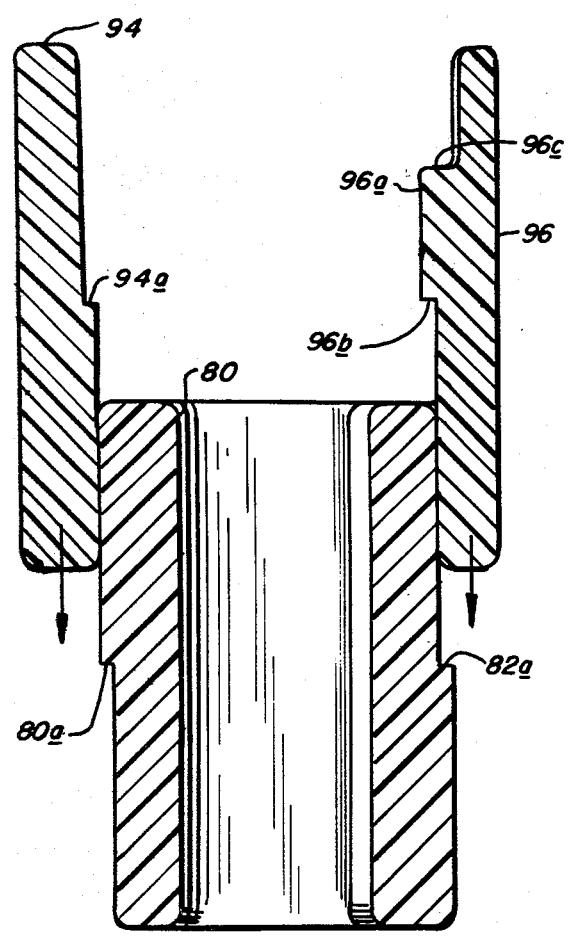
FIGS. 7a and 7b are sectional views taken along lines 7a—7a and 7b—7b of FIG. 6 showing the mating interconnection of the bracket and connector with FIG. 7a representing an initial insertion and FIG. 7b the locked position.

Referring to FIG. 7a, it will be seen that the ear 80 is provided with an undercut 80a, and the ear 82 includes a step 82a. The undercut and step are positioned generally opposite but slightly offset from each other and midway between the upper and lower ends of the ears.

The connector end 78 of the clamp 74 includes a base section 88 which extends transversely of the clamp body. Adjacent the edges of the base 88, there are angularly positioned wall portions 90 and 92 for engaging the outer terminal ends of the ears 80 and 82 which provide stability to the clamp in the horizontal and vertical planes.

Extending outwardly and slightly toward one another or converging to one another are a pair of ears 94 and 96 for interlocking engagement with the outer surfaces of ears 80 and 82. The converging shapes provide an inclined ramp-like effect which causes the clamp to be drawn toward the body and provide a secure connection. The ears 94 and 96 are intended to removably but securely engage the bracket ears 80 and 82 and also define a space 98 for cooperation in removal of the auxiliary clamp from the body.

Referring to FIG. 7a, the ear 94 is seen to include a step 94a, and the inner surface of ear 94 is shaped to matingly conform to the outer surface of the ear 80.

The ear 96 includes an inwardly-extending shoulder portion 96a that defines an undercut 96b and an upper step 96c which is larger than the undercut 96b. The undercut 96b is shaped to matingly conform with the step 82a, while the step 96c cooperates with the ear 82 to form a tool-receiving gap 98 for removing the clamp from the bracket.

In order to mount the clamp 74 on the bracket 70, the clamp 74 is positioned above the bracket 70. The clamp is then moved downward so that the inner surfaces of the ears 94 and 96 engage and slide against the outer surfaces of the bracket ears 82 and 84. As the clamp is moved downward, it slides against the outer surfaces of the bracket ears, until the leading end of the ear 96 engages the step 82a and the undercut 96b of the shoulder 96a engages the top of the ear 82. At that point the bracket and clamp flex with respect to each other so that the leading edge of the ear 96 rides over the step 82a and the undercut 96b moves past the top of the ear 82.

Figure 7B:
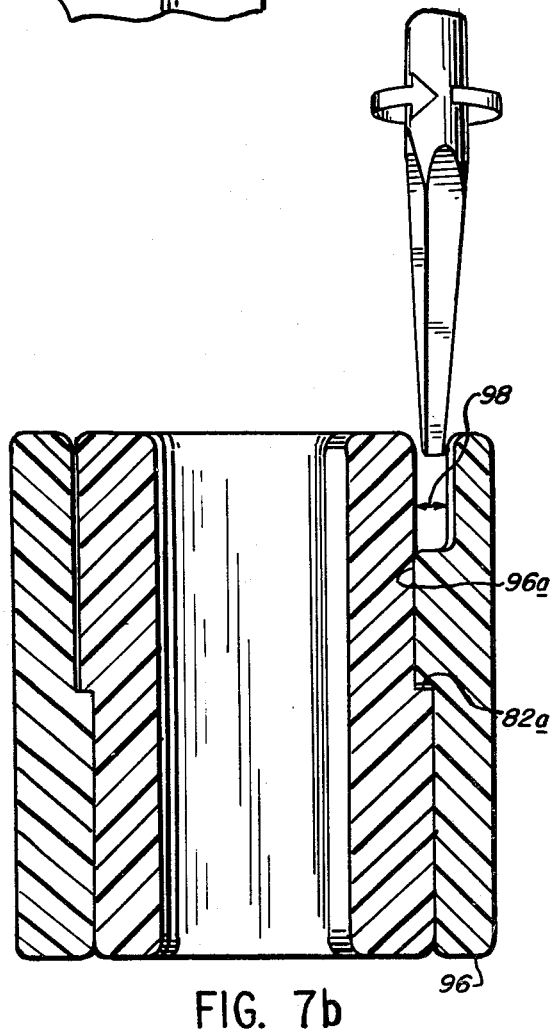

From there the clamp 74 can continue to move downwardly until the step 94a passes the undercut 80a, thereby allowing the ear 94 to snap inwardly and matingly engage the lower half of the ear 80. At about the same point, the undercut 96b is positioned adjacent the step 82a and the opposed positioning of the steps and undercuts (1) 94a and 80a and (2) 82a and 96b lock the clamp onto the bracket ears. As can be appreciated, once the steps and undercuts are in position, the clamp 74 is securely fixed to the bracket as shown in FIG. 7b.

In order to remove the clamp, a tool is placed within the gap 98, and the ear 96 is pried outwardly from ear 82 until the shoulder 96a can move downwardly past the step 82a. In that condition, the clamp 74 is pushed downwardly past the end of the bracket 70 for removal.

As previously explained, the housing may be mounted to the pole 12 so that the bracket 70 is either on one side or the other side of the pole. Due to the inverted and mirror-like shapes of the outer surfaces of the bracket ears 80 and 82, the bracket can be positioned on either side of the housing and still cooperate to engage and support a clamp, such as 74.

It will be appreciated that numerous changes and modifications can be made to the embodiment disclosed herein without departing from the spirit and scope of this invention.

What is claimed is:

1. A universal clamp assembly for use in supporting and grasping a medical appliance which includes: an elongated unitary housing having means for securing said assembly to a pole or other support; a pair of opposed arms having outer ends extending outwardly from said housing and which define a jaw for grasping an appliance, each of said arms having pivot point means for pivotally securing said arms to said housing and said arms being pivotally movable between an open position and a closed or grasping position; means cooperating with said arms for permitting said arms to be rotated about the axis of the housing; and rotatable biasing means carried in said housing and cooperating with said arms so as to resiliently bias said arms toward a closed or grasping position with a force sufficient to grasp a medical appliance placed between said arms and wherein each of said arms includes an inner portion extending inwardly into said housing and rearwardly from said pivot point means, and said biasing means including cam means for camming cooperation with the inner portion of each of said arm means, and spring means for urging said cam means against said inner portions of said arm means and causing said arm means to pivot and thereby cause said jaw to close and grasp said appliance.

2. A clamp assembly as in claim 1, wherein said cam means includes a disc-shaped member having means defining a pair of oppositely positioned sloping ramps for cammingly engaging the inner ends of said arms, said disc-shaped member being rotatably mounted within said housing rearwardly of said pivot and being rotatable with the rotation of said arms.

3. A clamp assembly as in claim 1, wherein said pivot means define a pivot axis transverse to the longitudinal axis of said housing.

4. A clamp assembly as in claim 1, wherein said means for securing said pole is substantially aligned with the longitudinal axis of said housing.

5. A universal clamp assembly for use in supporting and grasping a medical appliance which includes: an elongated unitary housing having means for securing said assembly to a pole or other support; a pair of opposed arms having outer ends extending outwardly from said housing and which define a jaw for grasping an appliance, each of said arms having pivot point means for pivotally securing said arms to said housing and said arms being pivotally movable between an open position and a closed or grasping position; means cooperating with said arms for permitting said arms to be rotated about the axis of the housing; and rotatable biasing means carried in said housing and cooperating with said arms so as to resiliently bias said arms toward a closed or grasping position with a force sufficient to grasp a medical appliance placed between said arms and wherein said means for permitting rotation of said arm comprises a disc-shaped pivot for cooperation with said pivot means on said arms to pivotally mount said arms with respect to said housing, said pivot means being rotatably mounted within said housing for rotation about the longitudinal axis of said housing, so that said arms are rotatable about said axis.

6. A clamp assembly as in claim 5, wherein said pivot means includes a disc-like portion having shoulder means defining a pair of opposed notches, and each of said shoulder means including rearwardly open pivot recess means so that one of said arm means is positionable in said notch and said pivot means of said arm are receivable in said pivot recess means.

7. A clamp assembly as in claim 5, wherein said pivot means define a pivot axis transverse to the longitudinal axis of said housing.

8. A clamp assembly as in claim 5, wherein said means for securing said pole is substantially aligned with the longitudinal axis of said housing.

9. A universal clamp assembly for use in supporting and grasping a medical appliance which includes: an elongated unitary housing having means for securing said assembly to a pole or other support; a pair of opposed arms having outer ends extending outwardly from said housing and which define a jaw for grasping an appliance, each of said arms having pivot point means for pivotally securing said arms to said housing and said arms being pivotally movable between an open position and a closed or grasping position; means cooperating with said arms for permitting said arms to be rotated about the axis of the housing; and rotatable biasing means carried in said housing and cooperating with said arms so as to resiliently bias said arms toward a closed or grasping position with a force sufficient to grasp a medical appliance placed between said arms and wherein said arms are replaceable so as to permit selection of arms having a size and shape effective for use with different medical appliances.

10. An interlocking bracket and clamp construction for removably securing a clamp to a bracket, (a) said bracket including a pair of outwardly extending and diverging ear-like members, each having a shaped outer surface, and each of said surfaces being an inverted mirror image of the other, with one of said surfaces shaped to provide a step and the other surface having an undercut and (b) said clamp having at one end a connector which includes a pair of outwardly extending and converging ears, each of said ears having inner surfaces for mating engagement with said bracket surfaces and for releasable securement to said bracket ears whereby said clamp and bracket may be secured to one another in a first attitude or in attitudes in which the relative positions of said bracket and clamp are reversed with respect to each other.

11. An interlocking bracket and clamp construction for removably securing a clamp to a bracket, (a) said bracket including a pair of outwardly extending and diverging ear-like members, each having a shaped outer surface, and each of said surfaces being an inverted mirror image of the other, with one of said surfaces shaped to provide a step and the other surface having an undercut and (b) said clamp having at one end a connector which includes a pair of outwardly extending and converging ears, each of said ears having inner surfaces for mating engagement with said bracket surfaces and for releasable securement to said bracket ears and wherein one of said clamp ear surfaces includes means defining a step as is adapted to matingly engage the bracket ear surface which includes an undercut, and the other of said clamp ear surfaces including means defining a shoulder with an undercut so that said other bracket surface is matingly engageable with said one surface with said step, so that the respective and mating undercuts oppose each other in a manner to releasably secure said clamp to said bracket.

12. A construction as in claim 11, wherein said clamp ears and said bracket ears are adapted to flex with respect to each other and position said undercuts and steps in positions opposed relative to each other.

13. A construction as in claim 12, wherein said other bracket ear which includes said shoulder includes a step formed by said shoulder positioned between said undercut and one end of said ear, whereby said clamp ear and said bracket ear define a tool-receiving gap for use in releasing said interlocking structure.

14. A universal clamp assembly for use in supporting and grasping a medical appliance which includes: an elongated unitary housing having means for securing said assembly to a pole or other support; a pair of opposed arms having outer ends extending outwardly from said housing and which define a jaw for grasping an appliance, each of said arms having pivot point means for pivotally securing said arms to said housing and said arms being pivotally movable between an open position and a closed or grasping position; means cooperating with said arms for permitting said arms to be rotated about the axis of the housing; and rotatable biasing means carried in said housing and cooperating with said arms so as to resiliently bias said arms toward a closed or grasping position with a force sufficient to grasp a medical appliance placed between said arms;
  wherein each of said arms includes an inner portion extending inwardly into said housing and rearwardly from said pivot point means, and said biasing means including cam means for camming cooperation with the inner portion of each of said arm means, and spring means for urging said cam means against said inner portions of said arm means and causing said arm means to pivot and thereby cause said jaw to close and grasp said appliance; and
  wherein said means for permitting rotation of said arm comprises a disc-shaped pivot for cooperation with said pivot means on said arms to pivotally mount said arms with respect to said housing, said pivot means being rotatably mounted within said housing for rotation about the longitudinal axis of said housing, so that said arms are rotatable about said axis.

15. A clamp assembly as in claim 14,
  wherein said pivot means includes a disc-like portion having shoulder means defining a pair of opposed notches, and each of said shoulder means including rearwardly open pivot recess means so that one of said arm means is positionable in said notch and said pivot means of said arm are receivable in said pivot recess means; and
  wherein said cam means includes a disc-shaped member having means defining a pair of oppositely positioned sloping ramps for cammingly engaging the inner ends of said arms, said disc-shaped member being rotatably mounted within said housing rearwardly of said pivot and being rotatable with the rotation of said arms.

* * * * *